(12) United States Patent
Bax

(10) Patent No.: US 6,214,359 B1
(45) Date of Patent: Apr. 10, 2001

(54) **USE OF A COMBINATION OF AMOXYCILLIN AND CLAVULANATE IN THE MANUFACTURE OF A MEDICAMENT FOR THE TREATMENT DRUG-RESISTANT *STREPTOCOCCUS PNEUMONIAE***

(75) Inventor: Richard Peregrine Bax, Westcott (GB)

(73) Assignee: SmithKline Beecham p.l.c., Middlesex (GB)

( * ) Notice: Subject to any disclaimer, the term of this patent is extended or adjusted under 35 U.S.C. 154(b) by 0 days.

(21) Appl. No.: 09/242,862

(22) PCT Filed: Aug. 19, 1997

(86) PCT No.: PCT/GB97/02235

§ 371 Date: Nov. 5, 1999

§ 102(e) Date: Nov. 5, 1999

(87) PCT Pub. No.: WO98/07424

PCT Pub. Date: Feb. 26, 1998

(30) Foreign Application Priority Data

Aug. 24, 1996 (GB) .................................................. 9617780

(51) Int. Cl.[7] ..................................................... A61K 9/00
(52) U.S. Cl. .......................... 424/400; 424/489; 424/497
(58) Field of Search ........................... 514/197; 424/464, 424/400, 489, 497

(56) References Cited

U.S. PATENT DOCUMENTS 4,537,887 * 8/1985 Rooke et al. ........................ 514/197

FOREIGN PATENT DOCUMENTS

WO 95 28927   2/1995  (WO) .
WO 96 24605   7/1996  (WO) .

OTHER PUBLICATIONS

Jacobsson,S., Fogh, A., Larsson,P., Lomborg,S. 1993. Evaluation of Amoxicillin Clavulanate Twice Daily versus Thrice Daily in the Treatment of Otitis Media in Children. Eur. J. Clin. Microbiol. Infect. Dis. (6): 319–324.*

Jacobsson et al., "Evaluation of Amoxicillin Clavulanate Twice Daily Versus Thrice Daily in the Treatment of Otitis Media in Children", *European Journal of Clinical Microbiology & Infectious Diseases,* 12(5), pp. 319–324 (1993).

Feldman et al., "Twice–Daily Antibotices in the Treatment of Acute Otitis Media:Trimethoprim–Sulfanethoxazole Versus Amoxicillian–Clauvulanate", *Canadian Medical Association Journal,* 142(2), pp. 115–118 (1990).

Hoberman et al., "Efficacy of amoxicillin/clavulanate for acute otitis media: relation to *Streptococcus pneuoniae* susceptibility", Pediatr Infect Dis J, vol. 15 No. 10, pp. 955–952, (1996).

* cited by examiner

*Primary Examiner*—Thurman K. Page
*Assistant Examiner*—Liliana Di Nola-Baron
(74) *Attorney, Agent, or Firm*—Dara L. Dinner; Stephen Venetianer; Charles M. Kinzig

(57) ABSTRACT

Infections potentially caused by DRSP may be treated by a method, which comprises administering to an adult or older child patient a pharmaceutical formulation comprising from 800 to 1100 mg amoxycillin and from 100 to 150 mg clavulanate in a weight ratio between 6:1 and 10:1 inclusive, in combination with a pharmaceutically acceptable carrier or excipient, three times a day (tid).

7 Claims, No Drawings

USE OF A COMBINATION OF AMOXYCILLIN AND CLAVULANATE IN THE MANUFACTURE OF A MEDICAMENT FOR THE TREATMENT DRUG-RESISTANT *STREPTOCOCCUS PNEUMONIAE*

"This application is the national stage of PCT/GB97/02235, filed Aug. 19, 1997, which application claims priority from the United Kingdom application 9617780.3, filed Aug. 24, 1996".

This invention relates to an empiric method of treatment for bacterial infections potentially caused by drug resistant *Streptococcus pneumoniae* using formulations comprising amoxycillin and a salt of clavulanic acid (hereinafter termed "clavulanate" unless a specific salt is identified).

The combination of amoxycillin and clavulanate is an effective empirical treatment for bacterial infections and may be administered by oral dosing, for instance in the form of tablets, and, for paediatric formulations, aqueous solutions or suspensions, typically as a flavoured syrup.

Clavulanate is a β-lactamase inhibitor and is included with the β-lactam antibiotic amoxycillin to counter a β-lactamase mediated resistance mechanism. Some microorganisms such as *Streptococcus pneumoniae* have resistance mechanisms which are not β-lactamase mediated. WO94/16696 discloses generally that potassium clavulanate may enhance the effectiveness of beta-lactam antibiotics such as amoxycillin against microorganisms having a resistance mechanism which is not β-lactamase mediated.

*Streptococcus pneumoniae* is an important pathogen in respiratory tract infection in the community. *S. pneumoniae* is the most commonly implicated bacterium in the important respiratory tract infections of otitis media in paediatrics and sinusitis in patients of all ages and acute exacerbations of bronchitis and pneumococcal pneumonia in adults. There have been increasing reports in Europe and the US of the emergence of DRSP (drug-resistant *Streptococcus pneumoniae*) with decreased suspectibility to β-lactam and other antibiotics.

Whilst confirmed cases of DRSP infection may be successfully treated with relatively high levels of amoxycillin, there still remains the need to develop effective empiric treatments, where DRSP may be suspected, for instance in an area with a high prevalence of DRSP, but where other, β-lactamase producing, organisms may also be present.

International Application WO 97/09042 (SmithKline Beecham Corp) (published after the priority date of the present application) describes formulations for treating DRSP comprising potassium clavulanate and amoxycillin characterised by a relatively high amount of amoxycillin and a twice daily (bid) dosage regimen. Preferred formulations comprise a ratio of 14:1(amoxycillin:clavulanate), with a typical dosage regimen for paediatrics being 90/6.4 mg/kg/day and for adults 3500/250 mg/day, taken as as two equal dosages, 12 hours apart (bid).

International Application WO 96/34605 (SmithKline Beecham plc/Corp) (published after the priority date of the present application) describes paediatric formulations comprising a 7:1 ratio of amoxycillin and clavulanate, for use in a twice daily dosing regimen (bid), such that the total daily dosage is 70/10 mg/kg/day.

International Application WO 95/28927 (SmithKline Beeecham Corp) describes tablets comprising 875 mg amoxycillin and 125 mg clavulanate, for use in a bid regimen, such that the total daily dosage is 1750/250 mg/day.

SmithKline Beecham markets in France a paediatric formulation ('Nourrisson') comprising amoxycillin and clavulanate in an 8:1 ratio for use in a thrice daily dosing regimen (tid), such that the total daily dosage is 80/10 mg/kg/day.

It has now been found that empiric treatment of infections potentially caused by DRSP may also be successfully treated with formulations of amoxycillin/clavulanate taken three times a day (tid), rather than two times a day, using a lesser ratio of amoxycillin to clavulanate.

Accordingly, the present invention provides a method of treatment of infections potentially caused by DRSP which method comprises administering to a patient in need thereof a pharmaceutical formulation adapted for oral administration comprising either:

for an adult or older child patient, from 2500 to 3250 mg/kg amoxycillin per day and from 350 to 400 mg/kg clavulanate per day in a weight ratio between 6:1 and 10:1 inclusive; or for a paediatric patient, from 75 to 125 mg/kg amoxycillin per day and from 12 to 18 mg/kg clavulanate per day in a weight ratio between 6:1 and 10:1 inclusive;

in combination with a pharmaceutically acceptable carrier or excipient.

Suitably, the method is used for the empiric treatment of infections, potentially caused by DRSP, in particular respiratory tract infections such as otitis media in paediatrics, sinusitis and pneumonia in patients of all ages and acute exacerbations of bronchitis in adults.

The invention also provides for the use of amoxycillin and clavulanate in the manufacture of a medicament for the empiric treatment of infections potentially potentially caused by DRSP which medicament comprises:

for an adult or older child patient, from 800 to 1100 mg amoxycillin and from 100 to 150 mg clavulanate in a weight ratio between 6:1 and 10:1 inclusive; or for a paediatric patient, from 30 to 40 mg/kg body weight of amoxycillin and from 3 to 8 mg/kg body weight of clavulanate in a weight ratio between 6:1 and 10:1 inclusive;

the medicament being taken three times a day (tid).

Suitably, the dosage is administered tid, for example in three, preferably equal, unit doses per day, suitably around eight hours apart.

The weight ratios of amoxycillin:clavulanate expressed herein are as free acid equivalent. Preferred amoxycillin:clavulanate ratios are between 6.5:1 to 7.5:1 inclusive, especially about 7:1 or between 7.5:1 and 8.5:1, especially about 8:1.

In the formulations of the invention the arnoxycillin is preferably in the form of amoxycillin trihydrate, although sodium amoxycillin, for example the crystalline form of sodium amoxycillin which is disclosed in EP 0131147 A may also be used.

Clavulanate is preferably in the form of potassium clavulanate. Potassium clavulanate is extremely moisture-sensitive and should be stored and handled in conditions of 30% RH or less, ideally as low as possible. Solid dosage forms should be packaged in atmospheric moisture-proof containers, and such forms and/or their containers may contain a desiccant.

Suitably, the dosage is administered in three, preferably equal, unit doses per day, suitably around 8 hours apart The formulations of the invention may be made up into solid dosage forms for oral administration by a method conventional to the art of pharmaceutical technology, e.g. tablets or powder or granular products for reconstitution into a suspension or solution. Suitable ingredients and suitable methods for making such tablets are disclosed in for example GB 2 005 538-A, WO 92/19227 and WO 95/28927. Powder or granular formulations, such as paediatric suspension formulations, may be manufactured using techniques which are generally conventional in the field of manufacture of pharmaceutical formulations and in the manufacture of dry formulations for reconstitution into such suspensions. For example a suitable technique is that of mixing dry powdered or granulated ingredients for loading into a suitable container.

For paediatric dosing, the formulations of the invention are preferably made up into a sweet flavoured aqueous syrup formulation of generally conventional formulation (except for its novel amoxycillin:clavulanate ratio and intended use) containing a suitable weight of the amoxycillin and clavulanate in a unit dose volume, e.g. 5 ml or 2.5 ml of the syrup. Because of the water-sensitivity of clavulanate it is preferred to provide such a syrup formulation as dry powder or granules contained in an atmospheric moisture-proof container or sachet for make up with water or other suitable aqueous medium shortly prior to use.

The formulation of this invention will normally, in addition to its active materials amoxycillin trihydrate and potassium clavulanate, also include excipients which are standard in the field of formulations for oral dosing and used in generally standard proportions, and at generally standard particle sizes and grades etc.

In the case of paediatric oral suspensions, these excipients may comprise suspending aids, glidants (to aid filling), diluents, bulking agent, flavours, sweeteners, stabilisers, and in the case of dry formulations for make up to an aqueous suspension, an edible desiccant to assist preservation of the potassium clavulanate against hydrolysis by atmospheric moisture on storage. Potassium clavulanate is normally supplied in admixture with silicon dioxide as diluent.

Suitable excipients for use include xantham gum (suspension aid), colloidal silica (glidant), succinic acid (stabiliser), aspartame (sweetener), hydroxypropylmethylcellulose (suspension aid) and silicon dioxide (desiccant, diluent for potassium clavulanate and bulking agent). Flavours may comprise common flavours such as orange, banana, raspberry and golden syrup, or mixtures thereof, to suit local requirements.

Generally the proportion of active materials amoxycillin trihydrate and potassium clavulanate in a dry formulation for make up with aqueous media into a solution, suspension or syrup formulation of the invention may be around 30–80 wt %.

The formulations of the invention may be adapted to paediatric dosing, i.e. to patients aged between 3 months to 12 years. Such formulations may be dosed in daily quantities up to the maximum normal permitted dose of amoxycillin and clavulanate.

A suitable dosage for paediatric patients is from 75 to 125 mg/kg amoxycillin per day and from 12 to 18 mg/kg clavulanate per day. Preferably, the dosage is 35±10%, especially ±5%, mg/kg amoxycillin and 5±10%, especially ±5%, mg/kg clavulanate (i.e. nominally a 7:1 ratio) administered tid.

A suitable dosage for older children and adult patients is from 2500 to 3250 mg/kg amoxycillin per day and from 350 to 400 mg/kg clavulanate per day. Preferably, the dosage is 875±10%, especially ±5%, mg amoxycillin and 125±10%, especially ±5%, mg clavulanate (i.e. nominally a 7:1 ratio), or 1000±10%, especially ±5%, mg amoxycillin and 125±10%, especially ±5%, mg clavulanate (i.e. nominally a 8:1 ratio), administered tid.

The formulation of the invention may for example be provided in solid unit dose forms embodying suitable quantities for the administration of such a daily dose. For example a unit dosage form may be tablets, or sachets containing granules or powders for reconstitution, one or two of which are to be taken at each tid dosing interval. Alternatively a unit dose may be provided as a bulk of solid or solution or suspension, e.g. as a syrup for paediatric administration, together with a suitable measuring device of known type to facilitate administration of a suitable unit dose quantity of the formulation. A suitable unit dose quantity is one which enables the administration of the above-mentioned daily dosage quantity divided between three tid doses.

For paediatric patients, a suitable unit dose quantity is preferably one which enables the administration of the above-mentioned daily dosage quantity in a volume of a solution or suspension suitable for oral administration to a paediatric patient, preferably of between 2.5 to 10 ml, preferably as a syrup. A paediatric formulation may therefore comprise a bulk of a solution or suspension, e.g. a syrup, or granules or powder which can be made up into such a solution or suspension, at a concentration of solution or suspension which contains such a dose in such a volume. Suitable such formulations are described in Intenational application no PCT EP96/01881 (SmithKline Beecham).

For adults, a suitable unit dose may be provided in a tablet. A suitable tablet comprising 875 mg amoxycillin and 125 mg clavulanate is marketed by SmithKline Beecham in several countries and is also described in WO 95/28927 (SmithKline Beecham).

EXAMPLE 1

Paediatric Formulation

The formulations listed below were prepared as dry powder mixtures, using conventional techniques. The proportions of ingredients are expressed as mg/5 ml dose of reconstituted aqueous suspension, the formulations nominally comprising either 200 or 400 mg of amoxycillin per 5 ml of dose:

| Ingredient | mg/5 ml | mg/5 ml |
| --- | --- | --- |
| amoxycillin trihydrate* | 408.0 | 204.0 |
| potassium clavulanate* | 61.56 | 30.78 |
| xanthan gum | 12.5 | 12.5 |
| colloidal silica | 25.0 | 25.0 |
| succinnic acid | 0.84 | 0.84 |
| flavour | 50.00 | 50.00 |
| aspartame | 12.50 | 12.50 |
| hydroxypropylmethylcellulose | 79.65 | 79.65 |
| silicon dioxide | to 885.5 | to 537.5 |

*expressed as free acid equivalent.

EXAMPLE 2

Tablet Formulation

A tablet formulation comprising 875 mg amoxycillin and 125 mg clavulanate was prepared having the following composition:

| Ingredient | mg | wt. % |
|---|---|---|
| Active Constituents: | | |
| Amoxycillin trihydrate | 1017.4 | 70.2 |
| (equivalent to amoxycillin) | 875.00 | |
| Potassium clavulanate | 152.45 | 10.5 |
| (equivalent to clavulanic acid) | 125.0 | |
| Other Constituents: | | |
| Magnesium Stearate | 14.50 | 1.00 |
| Sodium Starch Glycollate | 29.00 | 2.00 |
| Colloidal Silicon Dioxide | 10.0 | 0.70 |
| Microcrystalline Cellulose | 226.65 | 15.6 |
| Core tablet weight | 1450.00 | 100.00 |

The tablets are made by blending the amoxycillin, potassium clavulanate, and portions of microcrystalline cellulose and magnesium stearate, roller compacting this blend, then blending with the other constituents, before tabletting on a conventional tablet press and coating. The tablet core is coated with a film (Opadry White YS-1-7700/Opadry White OY-S-7300 ex Colorcon) from an aqueous solvent system, to give tablets with a nominal coated weight of 1482 mg. Further details of how the tablets are manufactured are provided in WO 95/28927 (SmithKline Beecham).

Similar tablets can be made in which the roller compaction step is replaced by slugging and/or a final film coating is applied from an organic solvent system such as dichloromethane rather than an aqueous solvent system.

What is claimed is:

1. A method of treatment of infections potentially caused by DRSP which method comprises administering to an adult or older child patient in need thereof a pharmaceutical formulation adapted for oral administration comprising from 800 to 1100 mg amoxycillin and from 100 to 150 mg clavulanate in a weight ratio between 6:1 and 10:1 inclusive in combination with a pharmaceutically acceptable carrier or excipient, three times a day (tid).

2. The method according to claim 1 in which the ratio of amoxycillin to clavulanate is between 6.5:1 and 7.5:1 inclusive or 7.5:1 to 8.5:1.

3. The method according to claim 1 in which the ratio of amoxycillin to clavulanate is about 7:1 or about 8:1.

4. The method according to claim 1 in which the dosage amount is 875±10% mg amoxycillin and 125±10% mg clavulanate or 1000±10% mg amoxycillin and 125±10% mg clavulanate.

5. The method according to claim 1 in which the formulation is in the form of tablets and adapted to provide about 875 mg amoxycillin and 125 mg clavulanate per unit dose.

6. The method according to claim 1 in which amoxycillin is in the form of amoxycillin trihydrate.

7. A method as claimed in claim 1 in which clavulanate is in the form of potassium clavulanate.

* * * * *